(12) United States Patent
Parthasarathy et al.

(10) Patent No.: US 6,469,437 B1
(45) Date of Patent: *Oct. 22, 2002

(54) HIGHLY TRANSPARENT ORGANIC LIGHT EMITTING DEVICE EMPLOYING A NON-METALLIC CATHODE

(75) Inventors: Gautam Parthasarathy, Princeton; Paul Burrows, Princeton Junction; Stephen R. Forrest, Princeton, all of NJ (US)

(73) Assignee: The Trustees of Princeton University, Princeton, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/964,863

(22) Filed: Nov. 5, 1997

Related U.S. Application Data

(60) Provisional application No. 60/064,005, filed on Nov. 3, 1997.

(51) Int. Cl.[7] ............................................. H05B 33/26
(52) U.S. Cl. ...................................... 313/504; 313/506
(58) Field of Search ............................. 313/503, 504, 313/506; 257/40; 372/96

(56) References Cited

U.S. PATENT DOCUMENTS

| | | | |
|---|---|---|---|
| 4,356,429 A | * 10/1982 | Tang | 313/503 |
| 5,203,974 A | 4/1993 | Kokado et al. | |
| 5,294,870 A | 3/1994 | Tang et al. | 313/504 |
| 5,424,560 A | 6/1995 | Norman et al. | 257/40 |
| 5,457,565 A | 10/1995 | Namiki et al. | 359/273 |
| 5,554,220 A | 9/1996 | Forrest et al. | 117/88 |
| 5,703,436 A | 12/1997 | Forrest et al. | 313/506 |
| 5,707,745 A | 1/1998 | Forrest et al. | 428/432 |
| 5,714,838 A | 2/1998 | Haight et al. | 313/506 |
| 5,881,089 A | * 3/1999 | Berggren et al. | 372/96 |
| 5,902,677 A | * 5/1999 | Shi et al. | 313/503 |
| 6,015,631 A | * 1/2000 | Park | 313/504 |
| 6,069,442 A | 5/2000 | Hung et al. | 313/504 |

FOREIGN PATENT DOCUMENTS

EP 0 704 915 4/1996

OTHER PUBLICATIONS

A Full–Color Thin Film EL Device With Two Stacked Substrates and Color Filters, S. Tanaka et al., Proceedings of the Society For Information Displays vol. 28 pp. 357–363, 1987 (No Month).*

Flat–Panel Displays and CRTs, L. Tannas, Jr. Van Nostrand Reinhold Company pp. 237–288, 1985 (No Month).*

C.W. Tang et al., Appl. Phys. Lett. 51, (Sep. 1987) Organic Electroluminescent Diodes pp. 913–915.

S.R. Forrest, P.E. Burrows and M.E. Thompson, Laser Focus World, Feb. 1995 Organc Emitters Promise a New Generation of Displays pp. 99–107.

(List continued on next page.)

Primary Examiner—Michael H. Day
(74) Attorney, Agent, or Firm—Kenyon & Kenyon

(57) ABSTRACT

Organic light emitting devices are disclosed which include a heterostructure for producing electroluminescence wherein the heterostructure includes a non-metallic cathode. As a representative embodiment of the present invention, the heterostructure for producing electroluminescence includes in order, a non-metallic cathode layer (1),
an electron injecting interface layer (6),
an electron transporting layer (2),
a hole transporting layer (3),
and an anode layer (4);

wherein the non-metallic cathode layer (1) includes an indium-tin oxide layer in contact with a copper phthalocyanine layer which functions as the electron injecting interface layer (6).

89 Claims, 12 Drawing Sheets

OTHER PUBLICATIONS

V. Bulovic, G. Gu, P.E. Burrows, M.E. Thompson, and S.R. Forrest, Nature 380, 29 (Mar. 1996) Transparent Light Emitting Devices.

V. Bulovic, P. Tian, P.E. Burrows, M.R. Gokhale, and S.R. Forrest, Appl. Phys. Lett. 70, 2954–2956 (Jun.1997) A Surface–Emitting Vacuum–Deposited Light Emitting Device.

Z. Shen, P.E. Burrows, V. Bulovic, S.R. Forrest, and M.E. Thompson, Science 276, (Jun. 1997) Three–Color, Tunable, Organic Light Emitting Devices pp. 2009–2011.

N. Karl, A. Bauer, J. Holzäofel, J. Marktanner, M. Möbus, and F. Stölzle, "Efficient Organic Photovoltaic Cells: The Role of Excitonic Light Collection, Exciton Diffusion to Interfaces, Internal Fields for Charge Separation, and High Charge Carrier Mobilities", Molecular Crystals and Liquid Crystals, vol. 252, pp. 243–258, 1994.

Whitlock, J.B., Panayotatos, P., Sharma, G.D., Cox, M.D., Savers, R.R., and Bird, G.R.; "Investigations of Materials and Device Structures for Organic Semiconductor Solar Cells," Optical Eng., vol. 32, No. 8, 1921–1934 (Aug. 1993).

P.E. Burrows, S.R. Forrest, Appl. Phys. Lett. 64, (Apr. 1994) Electroluminescence From Trap–Limitted Current Transport in Vaccuum pp. 2255–2287, B.H. Schechtman and W.E. Spicer, J. of Mol. Spec. 33 (1970) Near Infrared to Vacuum Ultraviolet Absorption Spectra of Phthalocyanine pp. 28–48.

P.E. Burrows, Z. Shen, V. Bulovic, D.M. McCarty, S.R. Forrest, J.A. Cronin and M.E. Thompson, J. Appl. Phys. 79, (May 1996) Relationship between Electroluminescence & Current Transport in Organic pp. 7991–8006.

S.R. Forrest, I.Y. Leu, F.F. So, and W.Y. Yoon, J. Appl. Phys. 66 (Dec. 1989) Opeical & Electrical Properties of Iosotype Crystalline Organic Hetrajunctions pp. 5908–5914.

A. Rajagopal, C.I. Wu, and A. Kahn, J. Appl. Phys. 83, (Mar. 1998) Energy Level Offset at Organic Semiconductors Hetrojunctions pp. 2649–2655.

K. Seki, Mol. Cryst. Liq. Cryst. 171, (1989) Ionization Energies of Free Molecules and Molecular Solids pp 255–270 (No month).

F.F. So and S.R. Forrest, J. Appl. Phys. 63, 442 (Jan. 1988) Dependence of the Electrical Characteristics of Organic r Inorganic G. Gu, V. Bulovic, P.E. Burrows, S.R. Forrest and M.E. Thompson, Appl. Phys. Lett. 68, (May 1996) Transparent Organic Light Emitting Devices pp. 2606–2608.

S.A. Van Slyke, C.H. Chen, and C.W. Tang, Appl. Phys. Lett. 69, 2160 (1996) Organic EL Devices With Improved Stability .

Parthasarathy, P.E. Burrows, V.G. Kozlov, and S.R. Forrest, "A Highly Transparent Organic Light Emitting Device Employing a Medal–Free Cathode," Poster Session Abstract, Materials Research Fair, Nov. 6, 1997, Princeton Materials Institute, Princeton University p. 18.

Stephen R. Forrest, "Ultrathin Organic Films Grown by Organic Molecular Beam Deposition and Related Techniques," Chemical Reviews, 97, 1793–1896 (Oct. 1997).

* cited by examiner

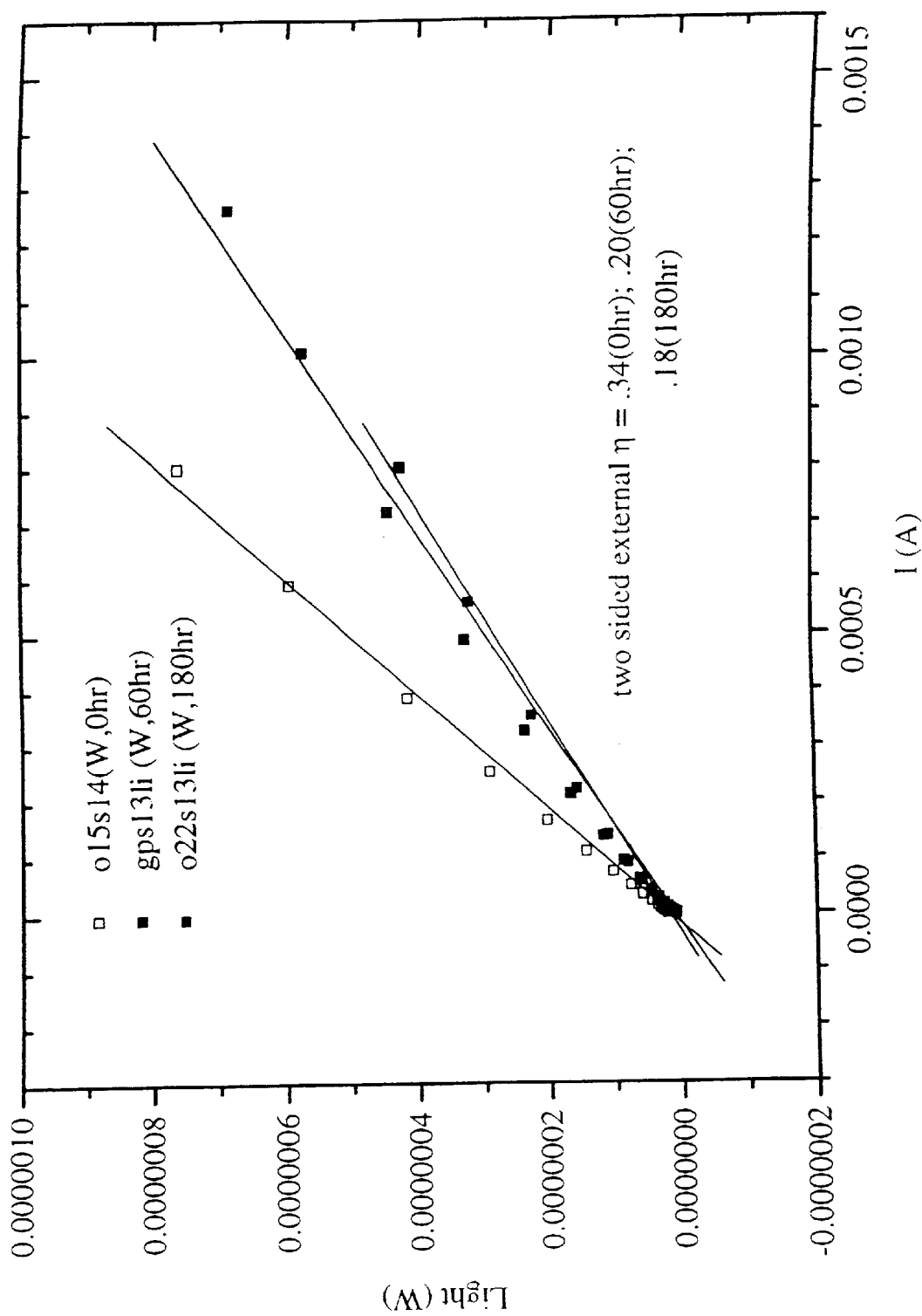

HIGHLY TRANSPARENT ORGANIC LIGHT EMITTING DEVICE EMPLOYING A NON-METALLIC CATHODE

This application claims the benefit of provisional application No. 60/064,005 filed Nov. 3, 1997.

GOVERNMENT RIGHTS

This invention was made with Government support under Contract No. F33615-94-1-1414 awarded by DARPA. The government has certain rights in this invention.

FIELD OF INVENTION

The present invention is directed to organic light emitting devices (OLEDs) that are comprised of a non-metallic cathode.

BACKGROUND OF THE INVENTION

OLEDs are comprised of several organic layers in which one of the layers is comprised of an organic material that can be made to electroluminesce by applying a voltage across the device, C. W. Tang et al., Appl. Phys. Lett 51, 913 (1987). Certain OLEDs have been shown to have sufficient brightness, range of color and operating lifetimes for use as a practical alternative technology to LCD-based full color flat-panel displays (S. R. Forrest, P. E. Burrows and M. E. Thompson, Laser Focus World, February 1995). Since many of the thin organic films used in such devices are transparent in the visible spectral region, they allow for the realization of a completely new type of display pixel in which red (R), green (G), and blue (B) emitting OLEDs are placed in a vertically stacked geometry to provide a simple fabrication process, a small R-G-B pixel size, and a large fill factor.

A transparent OLED (TOLED), which represents a significant step toward realizing high resolution, independently addressable stacked R-G-B pixels, was reported in International Patent Application No. PCT/US95/15790. This TOLED had greater than 71% transparency when turned off and emitted light from both top and bottom device surfaces with high efficiency (approaching 1% quantum efficiency) when the device was turned on. The TOLED used transparent indium tin oxide (ITO) as the hole-injecting electrode and a Mg—Ag—ITO electrode layer for electron-injection. A device was disclosed in which the ITO side of the Mg—Ag—ITO electrode layer was used as a hole-injecting contact for a second, different color-emitting OLED stacked on top of the TOLED. Each layer in the stacked OLED (SOLED) was independently addressable and emitted its own characteristic color. This colored emission could be transmitted through the adjacently stacked transparent, independently addressable, organic layer, the transparent contacts and the glass substrate, thus allowing the device to emit any color that could be produced by varying the relative output of the red and blue color-emitting layers.

The PCT/US95/15790 application disclosed an integrated SOLED for which both intensity and color could be independently varied and controlled with external power supplies in a color tunable display device. The PCT/US95/15790 application, thus, illustrates a principle for achieving integrated, full color pixels that provide high image resolution, which is made possible by the compact pixel size. Furthermore, relatively low cost fabrication techniques, as compared with prior art methods, may be utilized for making such devices.

Such devices whose structure is based upon the use of layers of organic optoelectronic materials generally rely on a common mechanism leading to optical emission. Typically, this mechanism is based upon the radiative recombination of a trapped charge. Specifically, OLEDs are comprised of at least two thin organic layers separating the anode and cathode of the device. The material of one of these layers is specifically chosen based on the material's ability to assist in injecting and transporting holes, a "hole transporting layer" (HTL), and the material of the other layer is specifically selected according to its ability to assist in injecting and transporting electrons, an "electron transporting layer" (ETL). With such a construction, the device can be viewed as a diode with a forward bias when the potential applied to the anode is more positive than the potential applied to the cathode. Under these bias conditions, the anode injects holes (positive charge carriers) into the hole transporting layer, while the cathode injects electrons into the electron transporting layer. The portion of the luminescent medium adjacent to the anode thus forms a hole injecting and transporting zone while the portion of the luminescent medium adjacent to the cathode forms an electron injecting and transporting zone. The injected holes and electrons each migrate toward the oppositely charged electrode. When an electron and hole localize on the same molecule, a Frenkel exciton is formed. Recombination of this short-lived state may be visualized as an electron dropping from its conduction potential to a valence band, with relaxation occurring, under certain conditions, preferentially via a photoemissive mechanism. Under this view of the mechanism of operation of typical thin-layer organic devices, the electroluminescent layer comprises a luminescence zone receiving mobile charge carriers (electrons and holes) from each electrode.

The materials that function as the electron transporting layer of the OLED are frequently the same materials that are incorporated into the OLED to produce the electroluminescent emission. Such devices in which the electron transporting layer functions as the emissive layer are referred to as having a single heterostructure. Alternatively, the electroluminescent material may be present in a separate emissive layer between the hole transporting layer and the electron transporting layer in what is referred to as a double heterostructure.

The material that is used as the cathode layer of an OLED has until now been comprised of a metal which has a low work function, for example, Mg:Ag. Such metallic cathode layers provide an electrically conductive path for current flow as well as a means of injecting electrons into the adjacent electron transporting layer. However, such metallic layers are also highly reflective and absorptive in the visible region of the spectrum.

This means that if a transparent OLED is desired, such as for stacked layers of a full-color SOLED or the single OLED of a monochromatic TOLED, a balance needs to be established between metallic layers that are thick enough to function as a cathode, but not so thick as to cause substantial light transmission or reflection losses. A conventional TOLED, therefore, uses 75–100 Å Mg:Ag capped with a thick layer of sputter-deposited ITO; the Mg:Ag layer serving both to inject electrons in $Alq_3$ and to protect it from the ITO sputtering. A device with about 70% transmission is obtained but there is still significant reflection from the compound cathode. In addition, in SOLED devices in which at least one of the color-producing layers is contained between the metallic cathodes of adjacent color-producing OLEDs, microcavity effects are present which give rise to color tuning problems. Such microcavity effects may also lead to an undesired angular dependence of the emitted light.

Furthermore, thin Mg:Ag layers are sensitive to atmospheric degradation and, therefore, require special designs and processing steps to be undertaken so as to preserve their effectiveness in functioning as the cathode of an OLED.

Although it would be desirable to overcome these light transmission and reflection problems by eliminating the metallic layers, until now it has not been known that a non-metallic cathode could be used in an organic light emitting device.

ADVANTAGES AND SUMMARY OF THE INVENTION

The present invention is directed to a highly transparent organic light emitting device (OLED) comprised of a non-metallic cathode.

More specifically, the present invention is directed to an OLED comprised of a semi-conducting material that functions as the non-metallic cathode.

Still more specifically, the present invention is directed to an OLED comprised of an inorganic semi-conducting material, such as ITO, that functions as the non-metallic cathode.

Yet more specifically, the present invention is directed to organic semiconducting lasers comprised of a non-metallic cathode.

In yet another aspect of the present invention, the OLED is comprised of a non-metallic cathode which is in contact with an organic layer that is capable of assisting in the injection and transport of electrons from the cathode to the luminescent zone of the OLED and that is, furthermore, capable of protecting the underlying organic layers from damage during deposition of the cathode layer. This "electron injecting interface layer" may be in direct contact with the electron transporting layer in the luminescent zone of the device or there may be an additional electron transporting layer between these two layers which further assists in transporting electrons to the luminescent zone of the OLED.

In addition, the present invention is directed to a method of fabricating an organic light emitting device comprised of a non-metallic cathode.

Further objectives and advantages of the present invention will be apparent to those skilled in the art from the detailed description of the disclosed invention.

BRIEF DESCRIPTION OF THE DRAWINGS

FIG. 3 shows the light output vs. current of an OLED as shown in FIG. 2a having an ITO cathode layer and a CuPc electron injecting interface layer. The lowest set of values in this figure was obtained at 180 hours.

DETAILED DESCRIPTION OF THE PREFERRED EMBODIMENTS

The present invention will now be described in detail for specific preferred embodiments of the invention, it being understood that these embodiments are intended only as illustrative examples and the invention is not to be limited thereto.

The present invention is directed to a new class of highly transparent organic light emitting devices (OLEDs) employing a non-metallic cathode. OLEDs that make use of a non-metallic cathode have a very low reflectivity and a high transparency that is close to the theoretical maximum that can be achieved for a multi-layer organic structure. The low-reflectivity of such OLEDs may be particularly beneficial for use in high contrast display applications as well as for use in eliminating microcavity effects in stacked organic light emitting devices (SOLEDs). OLEDs employing these low resistance non-metallic cathodes are expected to be particularly useful in reliable high-resolution full color flat panel displays, "heads-up" displays and organic-based lasers.

Figure 2A:
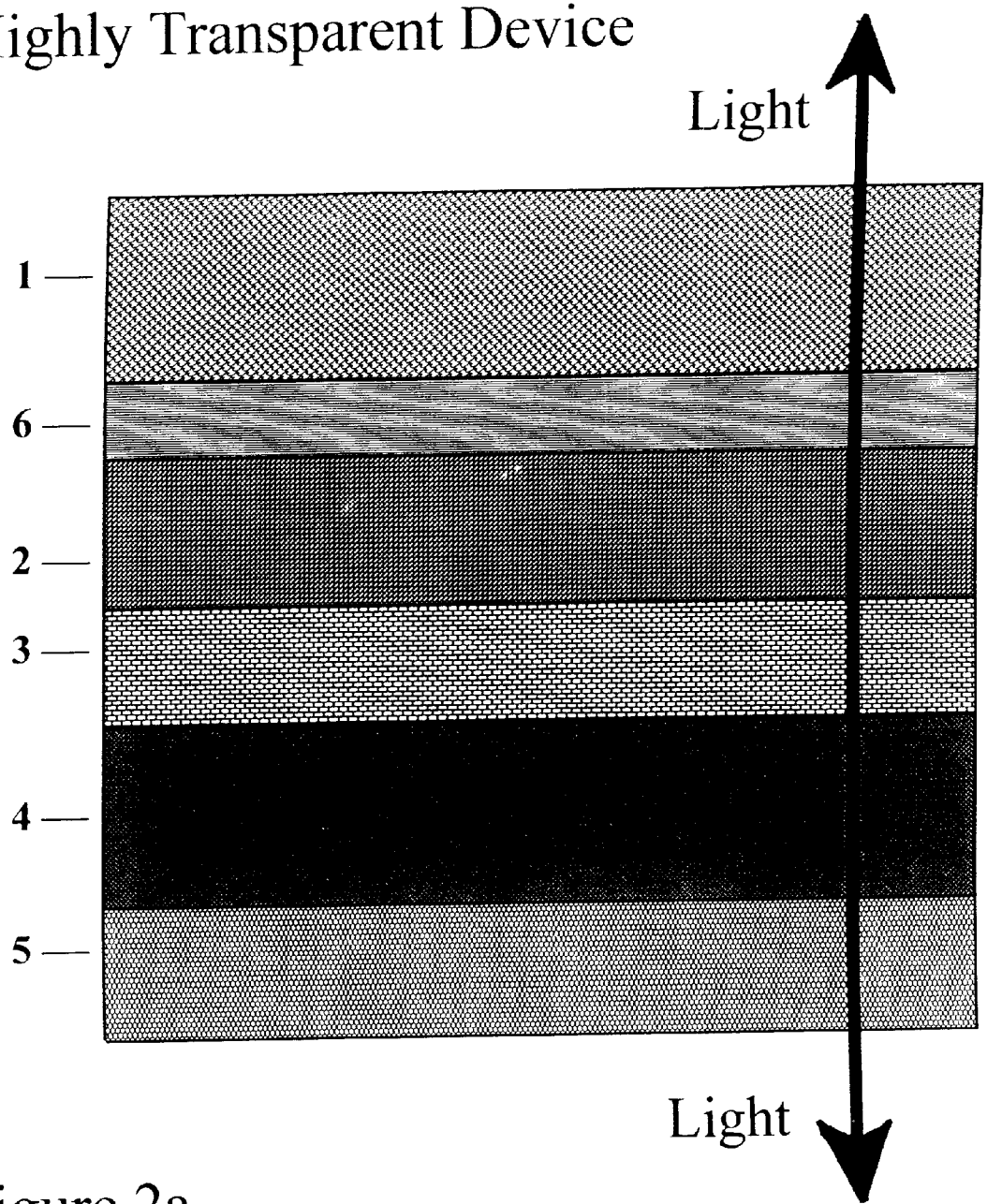
FIG. 2a shows an OLED having a non-metallic cathode 1, an electron injecting interface layer 6, an electron transporting layer 2, a hole transporting layer 3, an anode layer 4 and a substrate 5.
Figure 2B:
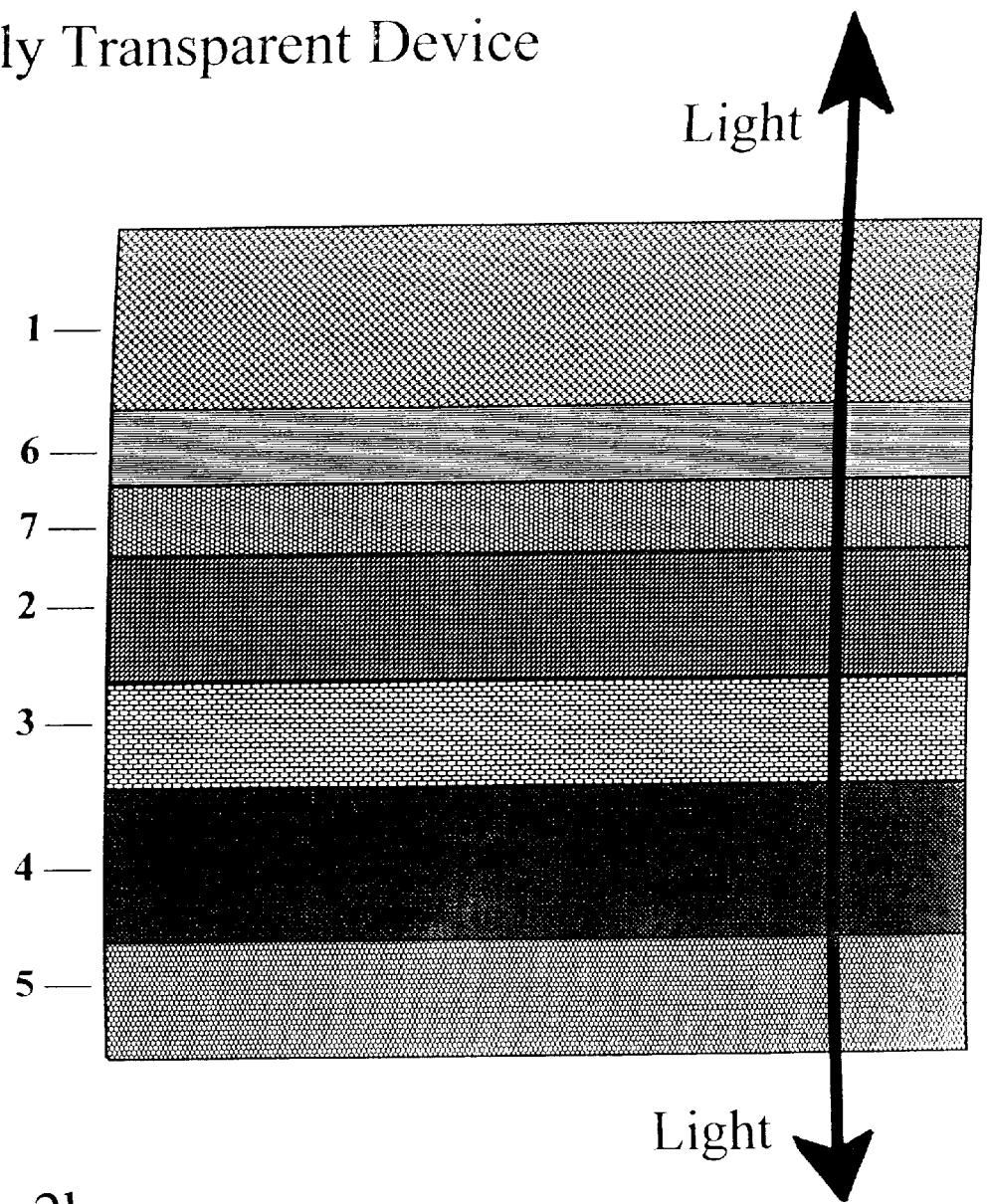
FIG. 2b shows an OLED having a non-metallic layer 1, an electron injecting interface layer 6, an intermediate electron transporting layer 7, an electron transporting layer 2, a hole transporting layer 3, an anode layer 4 and a substrate 5.

As a representative embodiment of the present invention as shown in FIG. 2a, a TOLED is deposited on a glass substrate pre-coated with a film of indium tin oxide (ITO) which serves as the transparent hole injecting anode. After depositing a hole transporting layer and an electron transporting layer, the electron injecting region is added by depositing, for example, a thin film of copper phthalocyanine (CuPc) which is then capped with a film of low-power, radio-frequency sputtered ITO. This second ITO layer functions as the cathode of this device. In addition to functioning, in some cases, as a protection layer that prevents damage to the underlying organic layers during the ITO sputtering process, the CuPc layer also functions in combination with the ITO layer as the electron injecting region for delivering electrons to the adjacent electron transporting layer. An additional intermediate electron transporting layer of 4,4'-di(N-carbazolo)diphenyl (CBP), for example, may be present between the first electron transporting layer and the CuPc layer, as shown in FIG. 2b.

The materials that may be effectively used in combination with the ITO layer to produce electron injection preferably have the following properties:

1. A chemical and structural stability that is sufficient to resist damage to sputtering during deposition of the ITO layer; large planar molecules such as phthalocyanines, naphthalocyanines and perylenes are representative examples. Derivatives of these compounds with further extended conjugation (e.g., additional fused benzo-, naphtha-, anthra-, etc., groups) may also be used.

2. An electron mobility that is sufficient to permit the layer to function as an electron transporting layer; an electron transporting material having a carrier mobility with a value of at least $10^{-6}$ cm$^2$/Vsec is generally believed to be sufficient for a material to function as an electron transporting layer, though substantially higher values are generally preferred; once again, large planar molecules such as the phthalocyanines and certain perylenes are representative examples.

3. The difference between the ionization potential (IP) and the HOMO/LUMO gap energy (the energy gap between the highest occupied molecular orbital and the lowest unoccupied molecular orbital), that is, the "IP-HOMO/LUMO gap energy", of the material used in the electron injecting interface layer is such that it is approximately equal to or preferably less than the IP-HOMO/LUMO gap energy of the film into which electrons are being injected. This guideline is not intended as a constraint that is to be strictly obeyed, but is instead intended to be approximately followed. For example, small deviations from this guideline of about 0.5 eV may be tolerated for certain combinations of materials. Use of this guideline helps to prevent formation of an energy barrier to electron flow into the contacted film (e.g. Alq$_3$).

Due to the absence of a metallic cathode layer, the representative Alq$_3$-based TOLEDs disclosed herein emit nearly identical light levels in the forward and back scattered directions with a total external quantum efficiency of about 0.3%. These devices are over 80% transmissive in the visible. The reflection and absorption characteristics, current-voltage, luminance-current, and electroluminescence spectra of OLEDs prepared according to the present invention demonstrate performance characteristics that are at least comparable with and in certain respects superior to conventional TOLEDs that employ a more reflective cathode comprised of a thin film of Mg:Ag capped with ITO.

Figure 4:
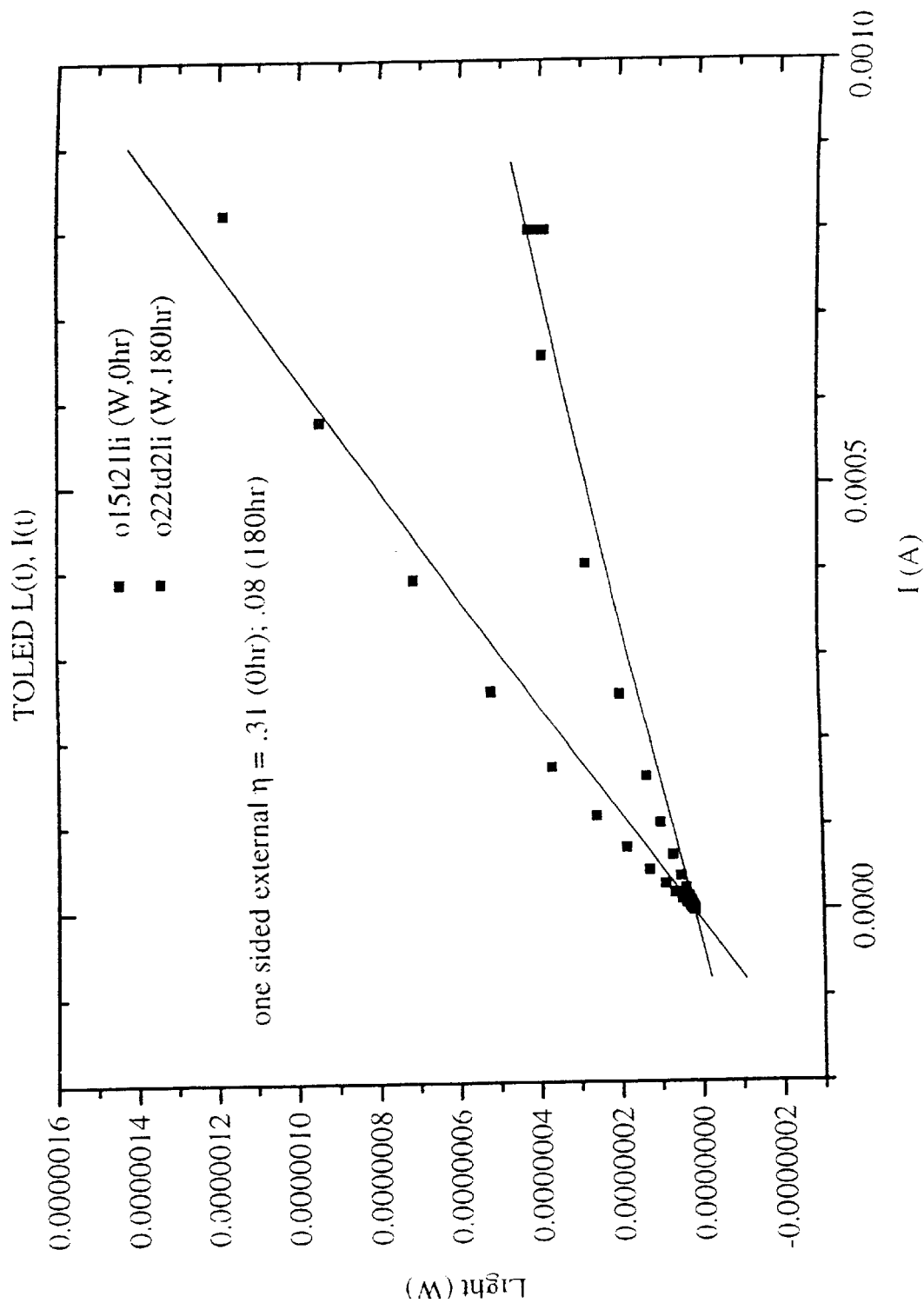
FIG. 4 shows the light output vs. current of a standard prior art TOLED device having an Mg:Ag cathode layer. The lower set of values in this figure was measured at 180 hours.
Figure 5:
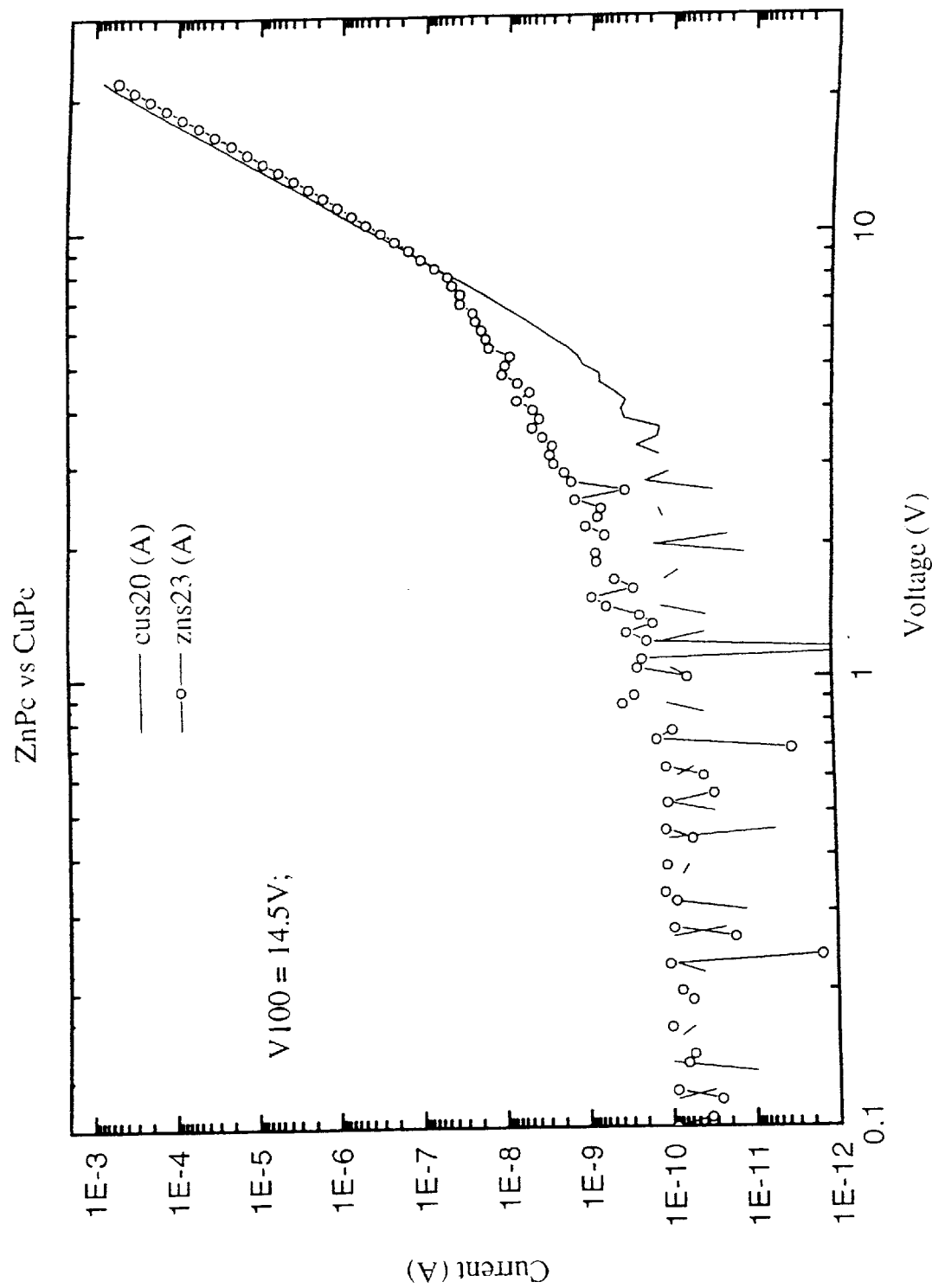
FIG. 5 shows the I–V curves for a ZnPc ("zns23") electron injecting interface layer and a CuPc (cus20") electron injecting interface layer.
Figure 6:
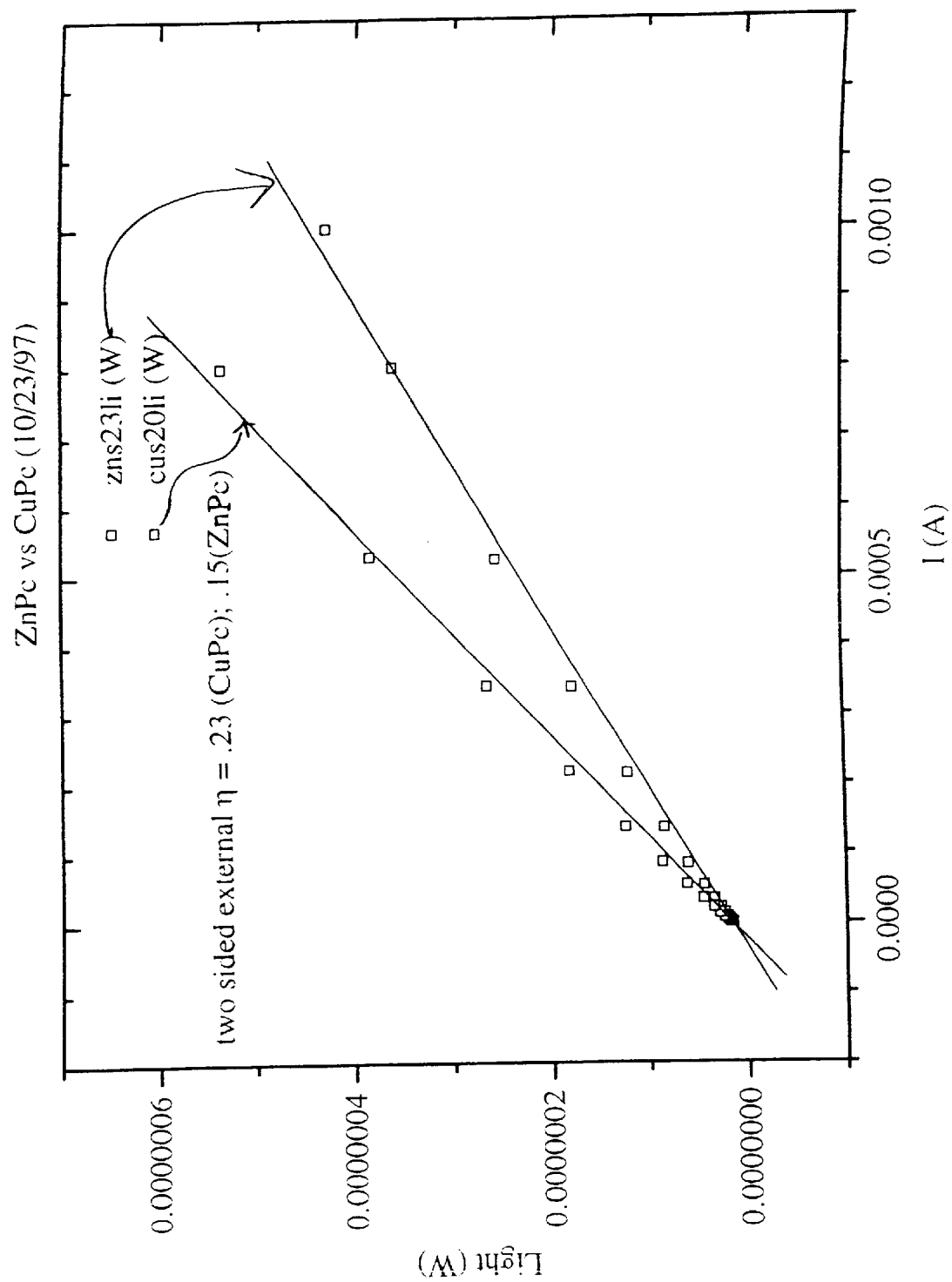
FIG. 6 shows the light output vs. current for a ZnPc ("zns23li") electron injecting interface layer as compared with a CuPc ("cu20li"), electron injecting interface layer where the efficiency η of the CuPc device was 0.23% and the ZnPc device was 0.15%.
Figure 7:
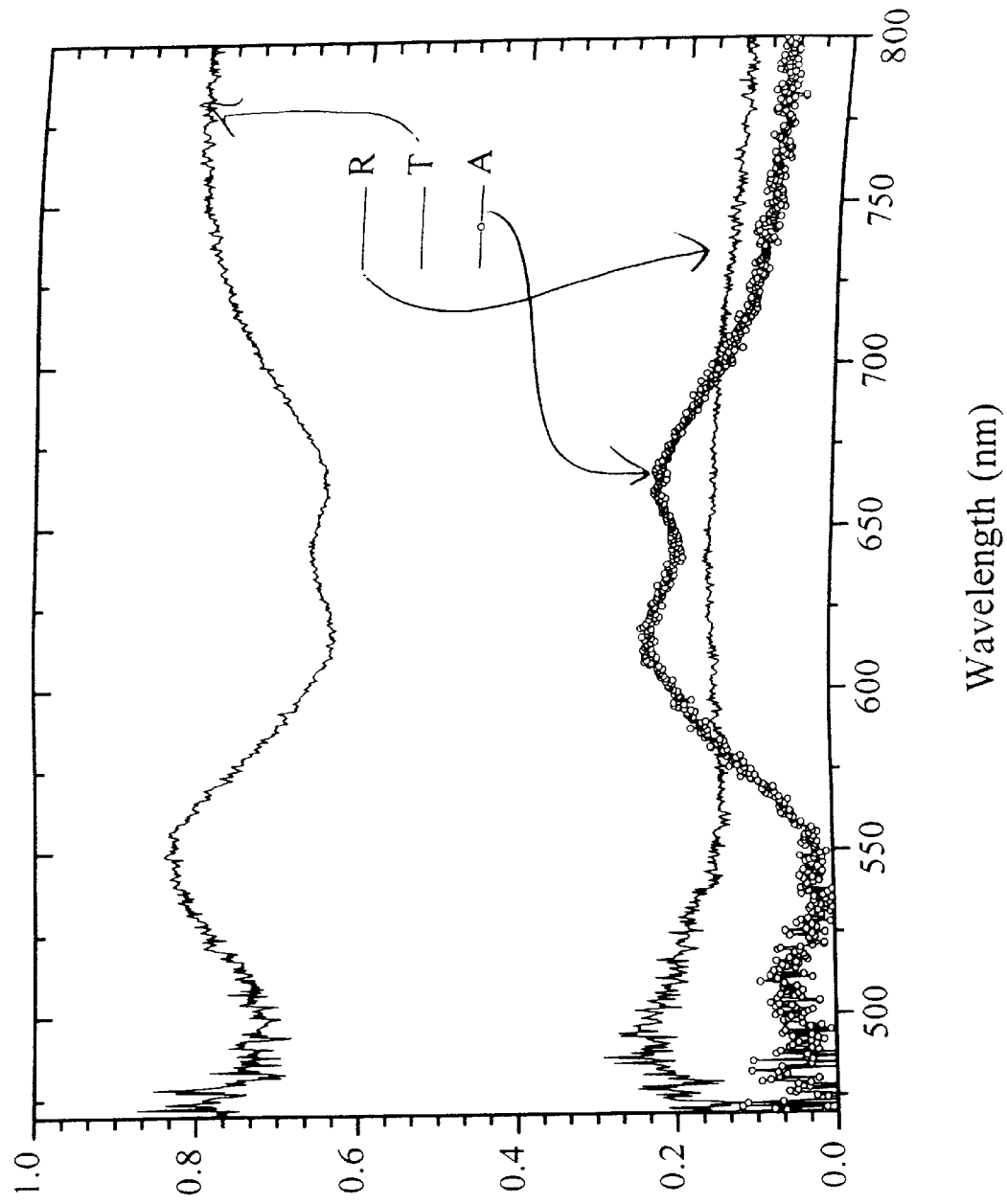
FIG. 7 shows the transmission (T), reflection (R) and absorption (A), as a function of wavelength (nm), of an OLED having an ITO cathode and CuPc electron injecting interface layer.
Figure 8:
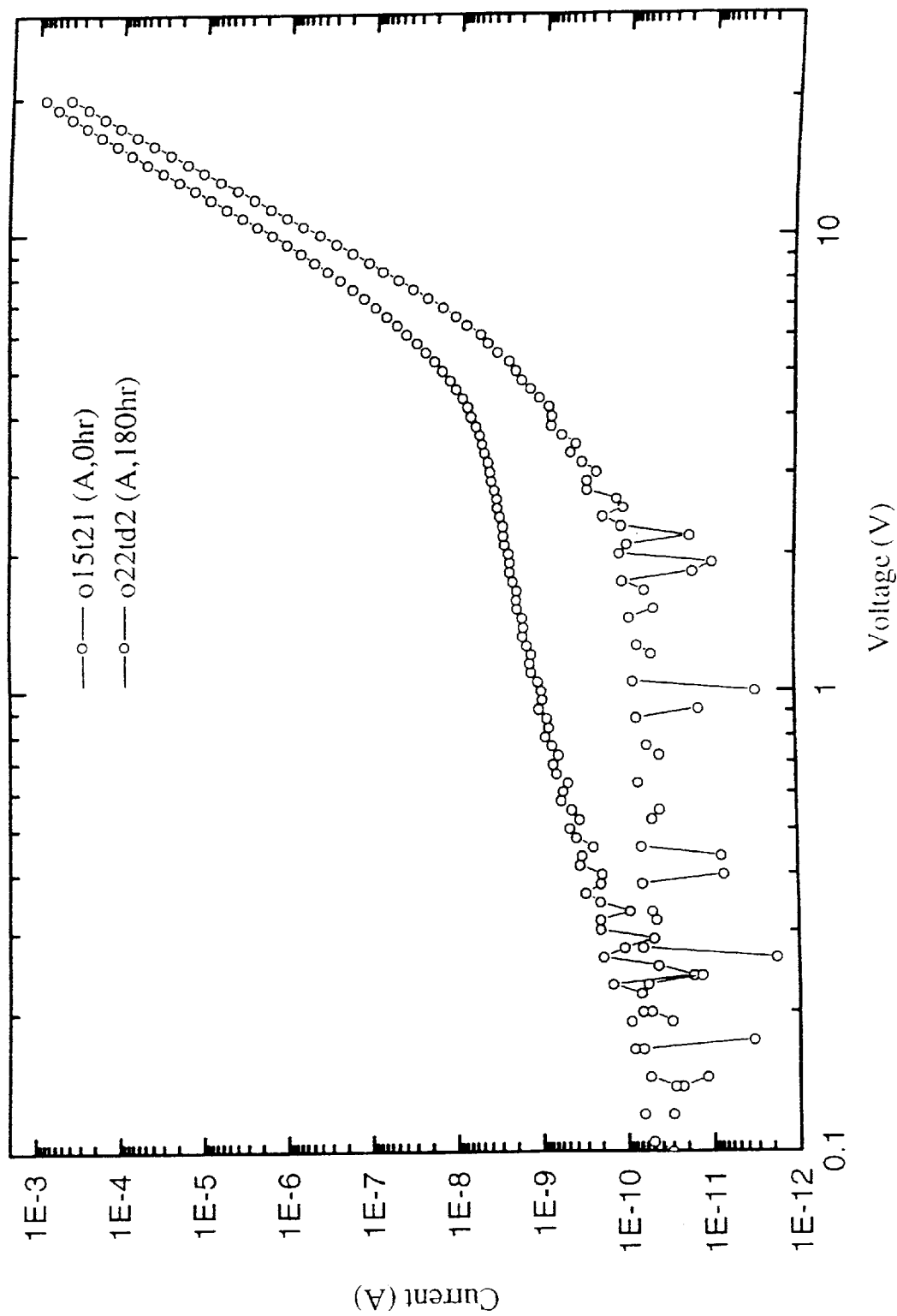
FIG. 8 shows the I–V characteristics of a standard prior art OLED having a metallic Mg:Ag cathode layer with the higher set of values at 0 hours and the lower set of values at 180 hours.
Figure 9:
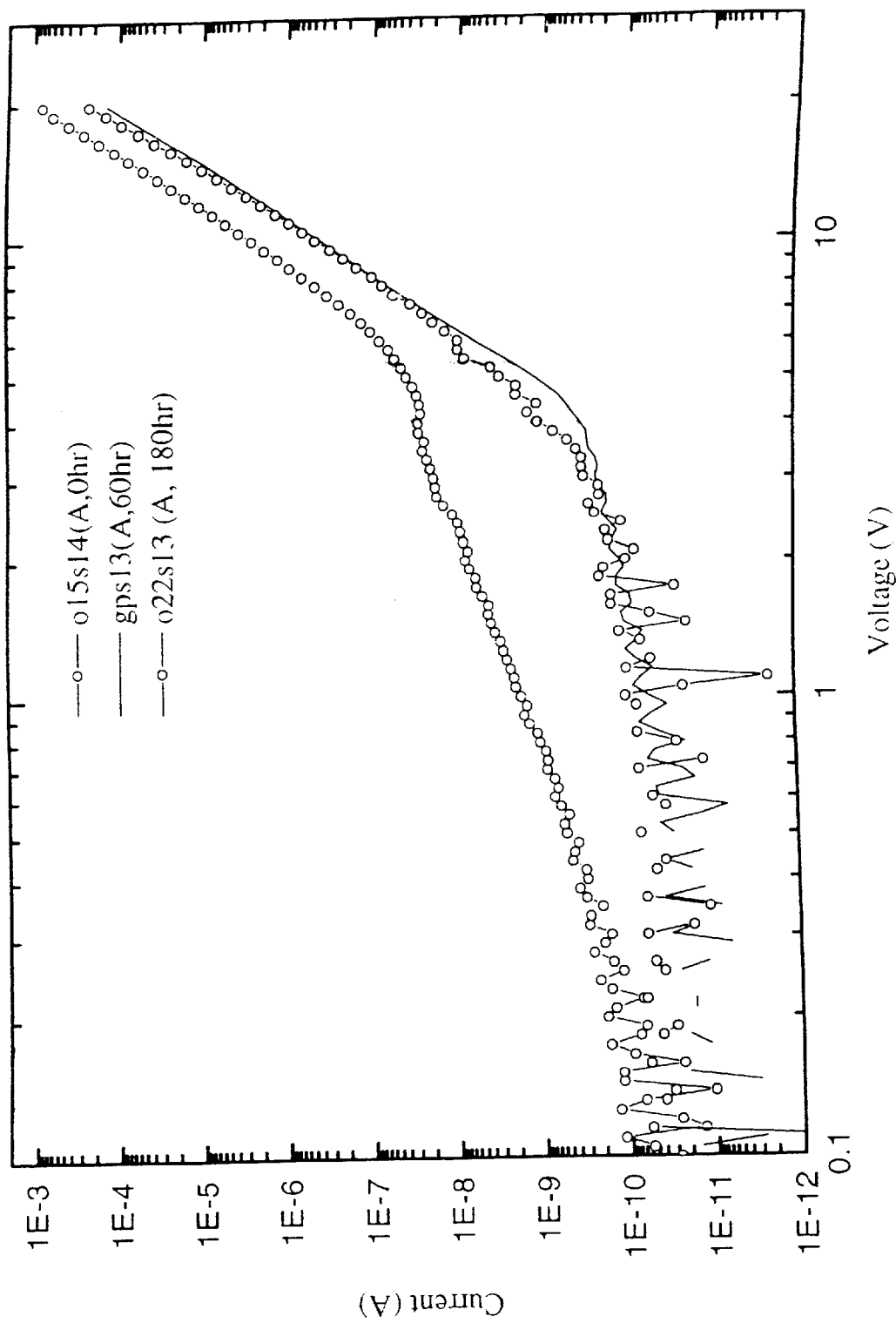
FIG. 9 shows the I–V characteristics of an OLED having an ITO cathode and a CuPc electron injecting interface layer with the higher set of values at 0 hours and the lower set of values at 60 and 180 hours.

For example, as shown by a comparison of the TOLED results shown in FIG. 3 with FIG. 4, TOLEDs according to the present invention show only about a 2-fold drop in light output at 180 hours, whereas prior art TOLEDs have about a 4-fold drop in light output over the same time interval. The results in FIG. 5 show that the phthalocyanines of both Cu (CuPc) and Zn (ZnPc) may be used as the electron injecting interface layer, though the results in FIG. 6 show that the CuPc device has a significantly higher quantum efficiency. A comparison of the results in FIG. 8 with the results in FIG. 9 shows that the stability of the I–V characteristics of OLEDs made according to the present invention is comparable to prior art devices. The results shown in FIG. 7 show that the total light transmission of an OLED made according to the present invention is near the theoretical maximum of what can be achieved for an OLED, except for that part of the spectrum which shows the Q-band absorption structure characteristic of CuPc. The reflection spectrum of this device approaches the theoretical minimum as limited by the glass/air and ITO/air interfaces. Anti-reflection layers can further reduce this reflection to a negligible value.

Figure 10:
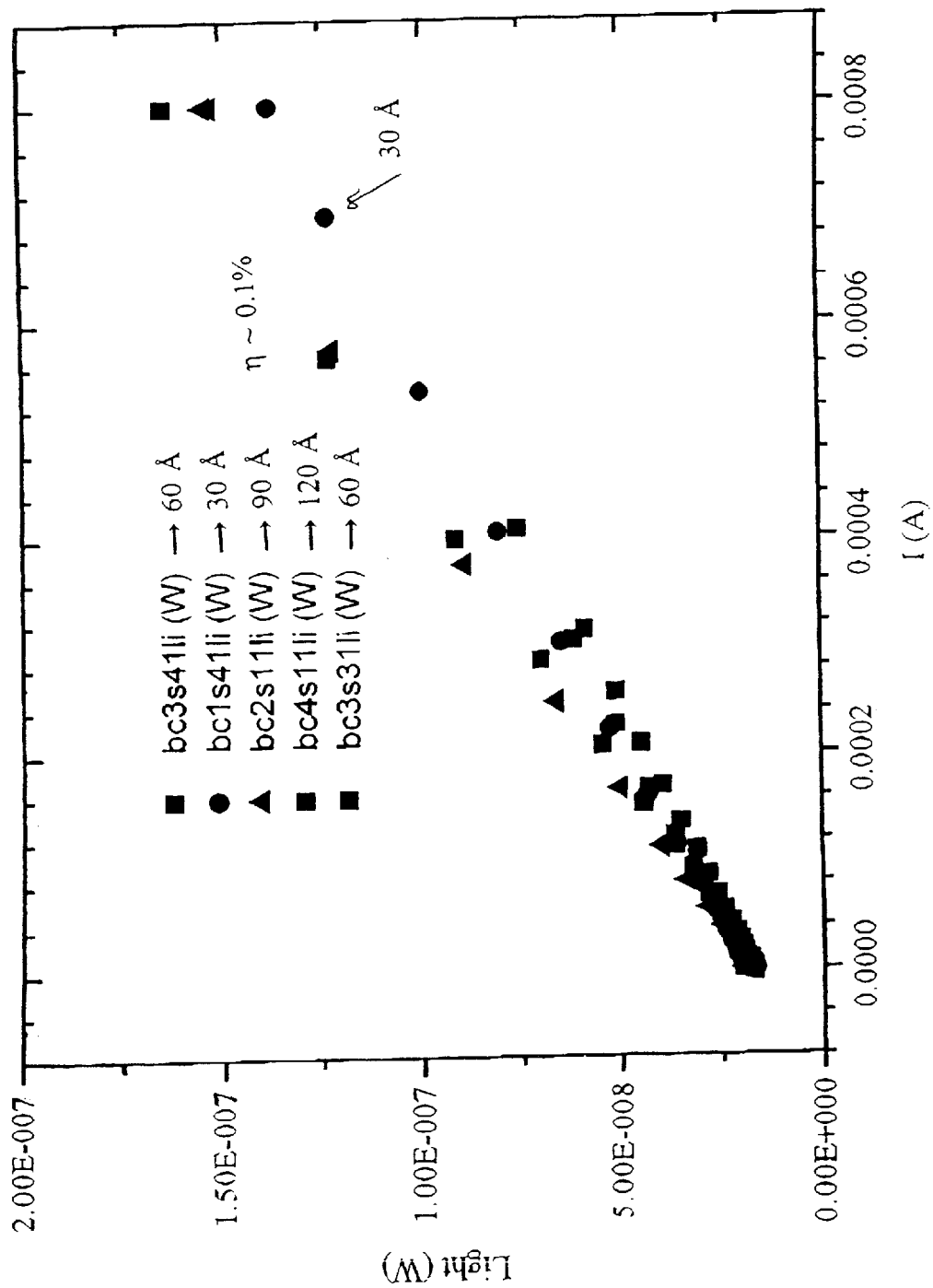
FIG. 10 shows the light output vs. current for devices having CuPc injection layer thicknesses from about 30 Å up to about 120 Å. These devices show a quantum efficiency η of about 0.1%.
Figure 11:
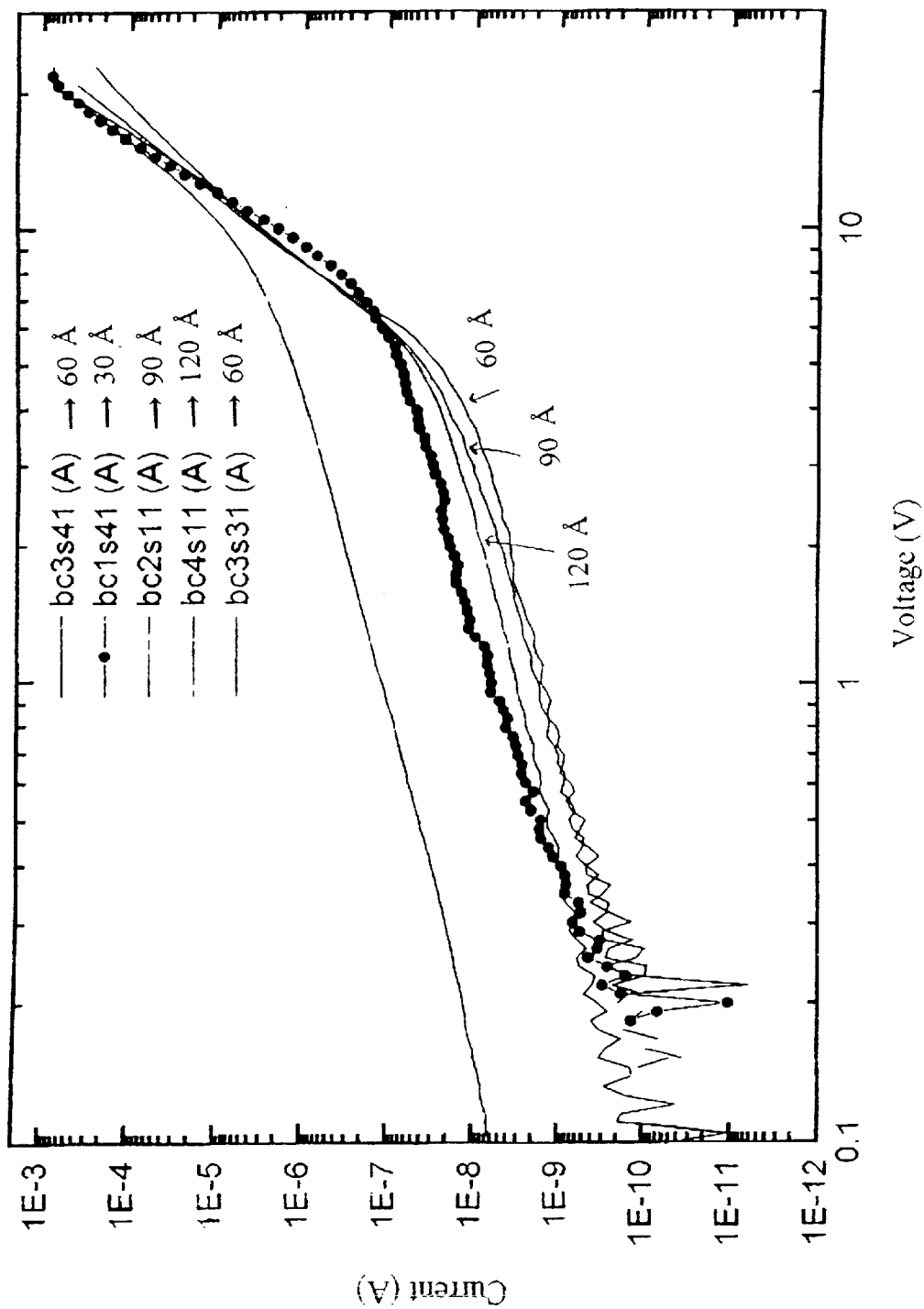
FIG. 11 shows the I–V characteristics of the devices of FIG. 10.

The electron injecting interface layer that is in contact with the ITO layer may have a thickness ranging from about 15–120 Å. For Example, FIGS. 10 and 11 show that whenever CuPc is used as the electron injecting interface layer, devices having a CuPc injection layer thickness from about 30 Å to about 120 Å produced comparable performance characteristics. The devices that were prepared to collect the data shown in FIGS. 10 and 11 also included a CuPc layer with a 50 Å thickness between the ITO anode layer and the hole transporting layer. This CuPc layer, which is in contact with the ITO anode layer, functions as a hole injection enhancement layer, such as disclosed in co-pending application having Ser. No. 08/865,491, filed May 29, 1997 (subsequently issued as U.S. Pat. No. 5,998,803).

As an example of another representative embodiment of the present invention, the non-metallic cathode may be used in a double heterostructure wherein, for example, an ITO layer is in direct contact with an organic layer which functions both as an electron transporting layer and as an interface layer, with this electron transporting and interface layer being in contact with a thin luminescent layer that is in contact with a hole transporting layer.

As still another representative embodiment in which the electron transporting layer is the emissive layer, the ITO layer may be in contact with an electron transporting and interface layer that is in direct contact with a hole transporting layer. In this case, the difference between the IP-HOMO/LUMO gap energy of the material used in the electron transporting and injecting layer is such that it is approximately equal to or preferably less than the IP-HOMO/LUMO gap energy of the material in the adjacent hole transporting layer and, in addition, the ionization potential of the material in the hole transporting layer is greater than the ionization potential of the material used in the electron transporting and interface layer.

As a representative embodiment of the invention in which the hole transporting layer is the emissive layer, the ITO layer may be in contact with an electron transporting and interface layer that is in direct contact with a hole transporting layer that produces the electroluminescence. In this case, the difference between the IP-HOMO/LUMO gap energy of the material used in the electron transporting and injecting layer is also such that it is approximately equal to or preferably less than the IP-HOMO/LUMO gap energy of the material in the adjacent hole transporting layer. However, in this case, the ionization potential of the material in the hole transporting layer is less than the ionization potential of the material used in the electron transporting and interface layer.

Thus, while the present invention is demonstrated for a single heterostructure in which the ITO layer is in contact with an electron injecting interface layer that is in contact with an electron transporting layer such as Alq$_3$, the present invention is directed toward any OLED comprised of a heterostructure for producing electroluminescence wherein the heterostructure includes a non-metallic cathode.

In addition, while the present invention is demonstrated with a semiconducting ITO layer as the non-metallic cathode, still other transparent conducting inorganic layers fall fully within the scope and spirit of the present invention. The term "non-metallic" embraces metals that may be present as one of the elements in a chemical compound, for example, as an oxide, but does not embrace materials comprised predominantly of the free metal nor does it embrace metal alloys.

In particular, the OLEDs of the present invention are comprised of a heterostructure for producing electroluminescence which may be fabricated as a single heterostructure or as a double heterostructure. The materials, methods and apparatus for preparing the organic thin films of a single or double heterostructure are disclosed, for example, in U.S. Pat. No. 5,554,220, which is incorporated herein in its entirety by reference. As used herein, the term "heterostructure for producing electroluminescence" refers to a heterostructure that includes, for a single heterostructure, in sequence, a hole injecting anode layer, a hole transporting layer, an electron transporting layer, and a cathode layer. An additional layer or layers may be present between one or more of the sequential pairs of these layers. For example, for a double heterostructure, a separate emissive layer is included between the hole transporting layer and the electron transporting layer. This separate emissive layer may be characterized as being a "thin luminescent layer." Alternatively, or in addition, a hole injection enhancement layer may be present between the anode layer and the hole transporting layer.

The hole injecting enhancement layer may in some cases be comprised of the same material, CuPc, as is used in the electron injecting and interface layer. In each case, the CuPc layer may be in direct contact with an ITO electrode, with the distinction between the two CuPc layers being that in one case the CuPc layer is in contact with an ITO layer that functions as an anode and in the other case the ITO layer functions as a cathode. In each case, the CuPc layer functions as a charge carrier and interface layer. On the one hand when in contact with the ITO anode, the CuPc layer assists in injecting and transporting holes from the anode to a hole transporting layer, and on. the other hand when in contact with the ITO cathode, the CuPc layer assists in injecting and transporting electrons from the cathode to an electrton transporting layer. The term "electron injecting interface layer" is used to refer to this layer that is present between and in contact with the cathode layer and the electron transporting layer of the heterostructure. The CuPc layer, in each case, may also function as a layer that protects any underlying organic layers, if present, from damage during the ITO deposition process. Whenever the ITO layer is present as the electrode in a SOLED structure, opposite faces of the ITO may function as an anode and cathode, respectively.

Either the anode layer or the cathode layer may be in contact with a substrate and each electrode is connected to electrical contacts which are capable of delivering a voltage across the device causing it to produce electroluminescence from either an electron transporting layer or a hole transporting layer. If the cathode layer is deposited on the substrate, the device may be referred to as having an inverted or IOLED structure. If the heterostructure for producing electroluminescence is included as part of a stacked OLED (SOLED), one or both of the electrodes of an individual heterostructure may be in contact with an electrode of an adjacent heterostructure. Alternatively, dependent on the circuitry used to drive the SOLED, an insulating layer may be provided between adjacent electrodes of two of the OLEDs in the stack.

While the present invention is directed to OLEDs comprised of non-metallic cathode layers rather than metallic cathode layers, the OLEDs of the present invention may, under certain circumstances, be used in combination with an OLED that does contain a metallic layer, for example, as the top or bottom OLED of a SOLED. In such cases, if the cathode layer is a metal cathode layer of Mg:Ag, a metal protective layer, for example, made of a layer of Ag for protecting the Mg:Ag cathode layer from atmospheric oxidation, may also be present.

The single or double heterostructures as referred to herein are intended solely as examples for showing how an OLED embodying the present invention may be fabricated without in any way intending the invention to be limited to the particular materials or sequence for making the layers shown. For example, the heterostructure typically includes a substrate which may be opaque or transparent, rigid or flexible, and/or plastic, metal or glass, in particular, a transparent polymer such as polyester, glass, sapphire or quartz, or substantially any other material that may be used as the substrate of an OLED.

Materials that may be used as the hole-injecting anode layer in a representative embodiment of the present invention include, in particular, ITO, Zn—In—$SnO_2$ or $SbO_2$, or substantially any other material that may be used as the hole-injecting anode layer of an OLED.

Materials that are present as a glass are desirable for use in the HTL of an OLED, rather than as a crystalline or polycrystalline material, since glasses are capable of providing higher transparency as well as producing superior overall charge carrier characteristics as compared with the polycrystalline materials that are typically produced when thin films of the crystalline form of the materials are prepared. Materials that may be used in the hole transporting layer in a representative embodiment of the present invention include, in particular, N,N'-diphenyl-N,N'-bis(3-methylpheny)1-1'biphenyl-4,4'diamine (TPD), 4,4'-bis[N-(1-naphthyl)-N-phenyl-amino]biphenyl ($\alpha$-NPD) or 4,4'-bis[N-(2-naphthyl)-N-phenyl-amino]biphenyl ($\beta$-NPD).

Materials that may be used as the electron transporting layer include, in particular, tris-(8-hydroxyquinoline)-aluminum ($Alq_3$), carbazole or 4,4'-di(N-carbazolo)diphenyl (CBP).

Materials that may be used as the separate emissive layer, if present, include, in particular, dye-doped $Alq_3$, or substantially any other material that may be used as the separate emissive layer of an OLED.

In those cases wherein the OLEDs of the present invention are used in combination with another OLED to form a SOLED structure that contains a metallic cathode layer, the materials that may be used as the electron-injecting, metallic cathode layer may include, in particular, Mg—Ag, Li—Ag or Ca, or substantially any other material that may be used as the metallic cathode layer of an OLED.

The insulating layer, if present, may be comprised of an insulating material such as $SiO_2$, $SiN_x$ or $AlO_2$, or substantially any other material that may be used as the insulating material of an OLED, which may be deposited by a variety of processes such as plasma enhanced chemical vapor deposition (PECVD), electron beam, etc.

The OLEDs of the present invention have the advantage that they can be fabricated entirely from vacuum-deposited molecular organic materials as distinct, for example, from OLEDs in which some of the layers are comprised of polymeric materials, which cannot be readily deposited using vacuum deposition techniques. A vacuum-deposited material is one which can be deposited in a vacuum typically having a background pressure less than one atmosphere, preferably about $10^{-5}$ to about $10^{-11}$ torr for vacuum deposition, or about 50 torr to about $10^{-5}$ torr for vapor deposition.

Although not limited to the thickness ranges recited herein, the substrate may be as thin as 10 $\mu$, if present as a flexible plastic or metal foil substrate, such as aluminum foil, or substantially thicker if present as a rigid, transparent or opaque, substrate or if the substrate is comprised of a silicon-based display driver; the ITO anode layer may be from about 500 Å (1 Å=$10^{-8}$ cm) to greater than about 4000 Å thick; the hole transporting layer from about 50 Å to greater than about 1000 Å thick; the separate emissive layer of a double heterostructure, if present, from about 50 Å to about 200 Å thick; the electron transporting layer from about 50 Å to about 1000 Å thick; and the non-metallic cathode layer from about 400 Å to greater than about 1500 Å thick with about 400–1000 Å being preferred, and about 500 Å still more preferred.

Thus, while there may be substantial variation in the type, number, thickness and order of the layers that are present, dependent on whether the device includes a single heterostructure or a double heterostructure, whether the device is a SOLED or a single OLED, whether the device is a TOLED or an IOLED, whether the OLED is intended to produce emission in a preferred spectral region, or whether still other design variations are used, the present invention is directed to those devices in which the OLED is comprised of a heterostructure for producing electroluminescence wherein the heterostructure includes a non-metallic cathode layer. As a representative embodiment of the present invention, an electron injecting interface layer may be present between and in contact with the cathode layer and the electron transporting layer of the heterostructure.

The present invention as disclosed herein may be used in conjunction with co-pending applications: "High Reliability, High Efficiency, Integratable Organic Light Emitting Devices and Methods of Producing Same", Ser. No. 08/774,119 (filed Dec. 23, 1996), now U.S. Pat. No. 6,046,543; "Novel Materials for Multicolor Light Emitting Diodes", Ser. No. 08/850,264 (filed May 2, 1997), now U.S. Pat. No. 6,045,930; "Electron Transporting and Light Emitting Layers Based on Organic Free Radicals", Ser. No. 08/774,120 (filed Dec. 23, 1996), now U.S. Pat. No. 5,811,833; "Multicolor Display Devices", Ser. No. 08/772,333 (filed Dec. 23, 1996), now U.S. Pat. No. 6,013,982; "Red-Emitting Organic Light Emitting Devices (OLED's)", Ser. No. 08/774,087 (filed Dec. 23, 1996), now U.S. Pat. No. 6,048,630; "Driving Circuit For Stacked Organic Light Emitting Devices", Ser. No. 08/792,050 (filed Feb. 3, 1997), now U.S. Pat. No. 5,757,139; "High Efficiency Organic Light Emitting Device Structures", Ser. No. 08/772,332 (filed Dec. 23, 1996), now U.S. Pat. No. 5,834,893; "Vacuum Deposited, Non-Polymeric Flexible Organic Light Emitting Devices", Ser. No. 08/789,319 (filed Jan. 23, 1997), now U.S. Pat. No. 5,844,363; "Displays Having Mesa Pixel Configuration", Ser. No. 08/794,595 (filed Feb. 3, 1997), now U.S. Pat. No. 6,091,195; "Stacked Organic Light Emitting Devices", Ser. No. 08/792,046 (filed Feb. 3, 1997), now U.S. Pat. No. 5,917,280; "High Contrast Transparent Organic Light Emitting Device Display", Ser. No. 08/821,380 (filed Mar. 20, 1997), now U.S. Pat. No. 5,986,401; "Organic Light Emitting Devices Containing A Metal Complex of 5-Hydroxy-Quinoxaline as A Host Material", Ser. No. 08/838,099 (filed Apr. 14, 1997), now U.S. Pat. No. 5,861,219; "Light Emitting Devices Having High Brightness", Ser. No. 08/844,353 (filed Apr. 18, 1997), now U.S. Pat. No. 6,125,226; "Organic Semiconductor Laser", Ser. No. 08/859,468 (filed May 19, 1997), now U.S. Pat. No. 6,111,902; "Saturated Full Color Stacked Organic Light Emitting Devices", Ser. No. 08/858,994 (filed May 20, 1997), now U.S. Pat. No. 5,932,895; "An Organic Light Emitting Device Containing a Hole Injection Enhancement Layer", Ser. No. 08/865,491 (filed May 29, 1997), now U.S. Pat. No. 5,998,803; "Plasma Treatment of Conductive Layers", PCT/US97/10252, (filed Jun. 12, 1997); "Patterning of Thin Films for the Fabrication of Organic Multi-color Displays", PCT/US97/10289, (filed Jun. 12, 1997); "OLEDs Containing Thermally Stable Asymmetric Charge Carrier Materials", Ser. No. 08/925,029, filed Sep. 8, 1997, now U.S. Pat. No. 6,242,115; "Light Emitting Device with Stack of OLEDS and Phosphor Downconverter", Ser. No. 08/925,403, (filed Sep. 9, 1997), now U.S. Pat. No. 5,874,803; "An Improved Method for Depositing Indium Tin Oxide Layers in Organic Light Emitting Devices", Ser. No. 08/928,800 (filed Sep. 12, 1997), now U.S. Pat. No. 5,981,306; and "Azlactone-Related Dopants in the Emissive Layer of an OLED", Ser. No. 08/948,130 (filed Oct. 9, 1997), now U.S. Pat. No. 6,030,715; each co-pending application or patent being incorporated herein by reference in its entirety. The subject invention may also be used in conjunction with the subject matter of each of co-pending U.S. patent application Ser. Nos. 08/354,674, now U.S. Pat. No. 5,707,745; 08/613,207, now U.S. Pat. No. 5,703,436; 08/632,322, now U.S. Pat. No. 5,757,026 and 08/693,359 and provisional patent application Ser. Nos. 60/010,013, now U.S. Pat. No. 5,986,268, 60/024,001, now U.S. Pat. No. 5,844,363, 60/025,501, now U.S. Pat. No. 6,125,226, 60/046,061, now U.S. Pat. No. 6,111,902 and 60/053,176, now U.S. Pat. No. 6,160,828, each of which is also incorporated herein by reference in its entirety.

The materials that may be used as the substrate, the hole-injecting anode layer, the hole transporting layer, the electron transporting layer, the separate emissive layer, if present, or the insulating layer, if present, include the materials as disclosed in these co-pending applications.

The OLED of the present invention may be used in substantially any type of device which is comprised of an OLED, for example, in OLEDs that are incorporated into a larger display, a vehicle, a computer, a television, a printer, a large area wall, theater or stadium screen, a billboard or a sign.

This invention will now be described in detail with respect to showing how certain. specific representative embodiments thereof can be made, the materials, apparatus and process steps being understood as examples that are intended to be illustrative only. In particular, the invention is not intended to be limited to the methods, materials, conditions, process parameters, apparatus and the like specifically recited herein.

AN EXAMPLE OF THE INVENTION

OLEDs were prepared using known procedures except that the OLEDs included a non-metallic ITO cathode layer rather than a metallic cathode layer. In addition, an electron injecting interface layer was present between the ITO cathode and an $Alq_3$ electron transporting layer. The ITO/Borosilicate substrates that were obtained commercially had an ITO thickness of about 1500 Å. The organic layers were thermally deposited in a standard bell-jar evaporator at pressures of $1\times10^{-6}$ torr. The alpha-NPD layer was deposited at a thickness of about 350 Å, the $Alq_3$ electron transporting layer was deposited at a thickness of about 450 Å and the copper phthalocyanine (CuPc) or zinc phthalocyanine (ZnPc) were deposited at a thickness of about 60 Å. The top ITO cathode layer was RF sputter-deposited at low powers and had a thickness of about 650 Å. OLEDs were also prepared containing a CBP layer between the CuPc layer and the $Alq_3$ layer. Such OLEDs showed performance characteristics comparable to the OLEDs in which no CBP layer was present.

The devices were characterized by measuring the current-voltage, luminance-current, electroluminescence spectra and the transmission, reflection and absorption spectra. Representative data are shown in FIGS. 3–11.

Figure 1:
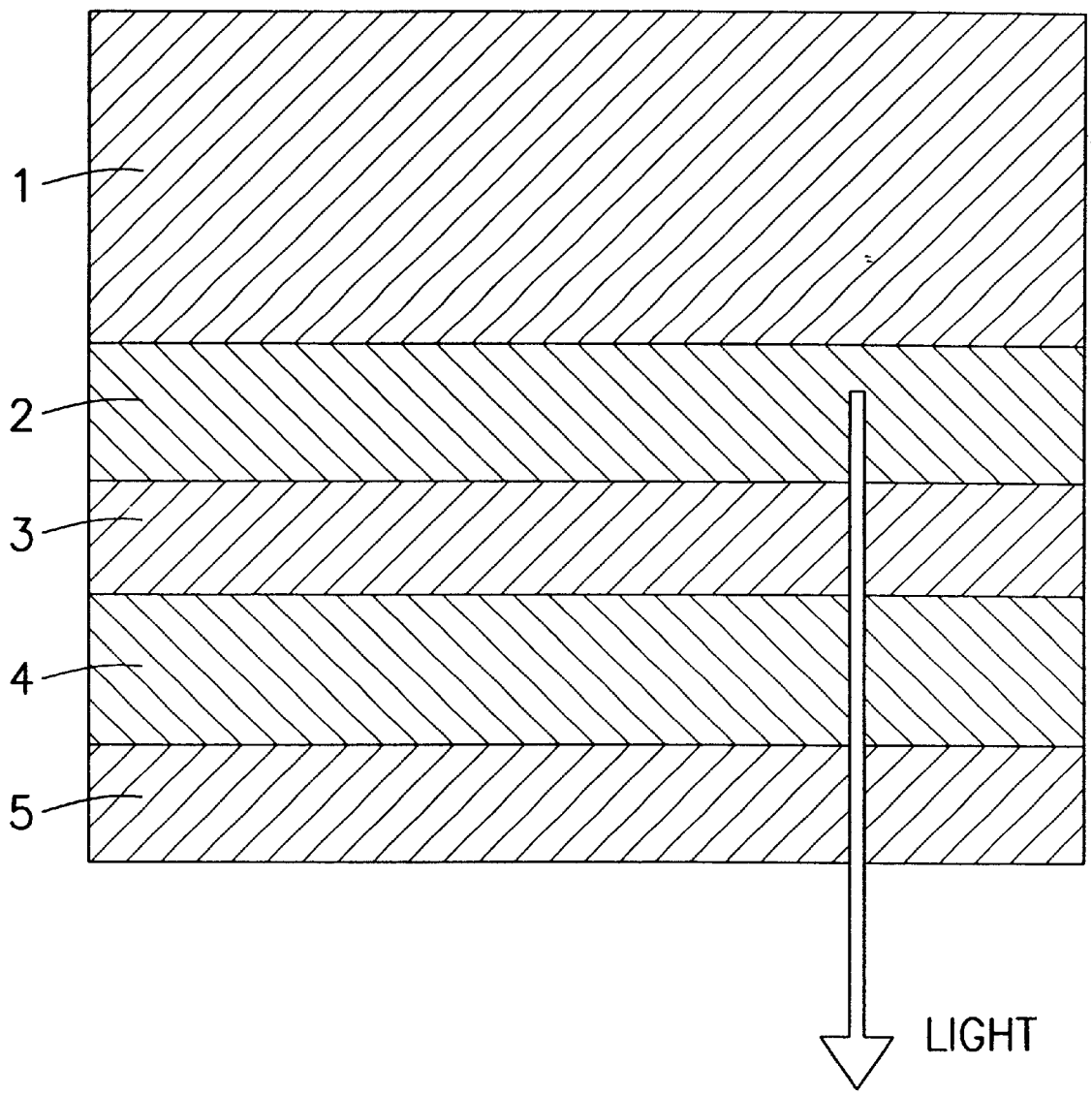
FIG. 1 shows a standard prior art device having a metallic Mg:Ag cathode layer 1, an electron transporting layer 2, a hole transporting layer 3, an anode layer 4 and a substrate 5.

The results were compared with a standard OLED, for example, as shown in FIG. 1 wherein the alpha-NPD hole transporting layer had a thickness of about 350 Å, the $Alq_3$ electron transporting layer had a thickness of about 450 Å and the Mg:Ag cathode layer had a thickness of about 1500 Å.

What is claimed is:

1. An organic light emitting device comprising a heterostructure for producing electroluminescence wherein the heterostructure includes a non-metallic cathode comprising a transparent semi-conducting inorganic material in direct contact with a conductive organic layer, wherein said conductive organic layer comprises a phthalocyanine.

2. The organic light emitting device of claim 1 wherein said transparent semi-conducting inorganic material comprises indium tin oxide.

3. The organic light emitting device of claim 2 wherein the heterostructure for producing electroluminescence is further comprised of, in order:
    a substrate;
    said non-metallic cathode;
    a second electron transporting layer;
    a first electron transporting layer;
    a hole transporting layer; and
    an anode layer.

4. The organic light emitting device of claim 3 wherein said second electron transporting layer comprises 4,4'-di(N-carbazolo)diphenyl.

5. The organic light emitting device of claim 1, wherein said phthalocyanine comprises copper phthalocyanine.

6. The organic light emitting device of claim 1 wherein said phthalocyanine comprises zinc phthalocyanine.

7. An organic light emitting device comprising a heterostructure for producing electroluminescence wherein the heterostructure includes a non-metallic cathode comprising a transparent semi-conducting inorganic material in direct contact with a conductive organic layer, wherein the heterostructure for producing electroluminescence is further comprised of, in order,
    an anode layer,
    a hole transporting layer,
    an electron transporting layer,
    an electron injecting interface layer, and
    said non-metallic cathode.

8. The organic light emitting device of claim 7 wherein said non-metallic cathode is comprised of indium tin oxide.

9. The organic light emitting device of claim 7 wherein said anode layer is in contact with a substrate.

10. The organic light emitting device of claim 9 wherein said substrate is transparent.

11. The organic light emitting device of claim 7 wherein said non-metallic cathode is in contact with a substrate.

12. The organic light emitting device of claim 11 wherein said substrate is transparent.

13. A display incorporating the organic light emitting device of claim 7.

14. A heads-up display incorporating the organic light emitting device of claim 7.

15. A flat panel display incorporating the organic light emitting device of claim 7.

16. A vehicle incorporating the organic light emitting device of claim 7.

17. A computer incorporating the organic light emitting device of claim 7.

18. A television incorporating the organic light emitting device of claim 7.

19. A printer incorporating the organic light emitting device of claim 7.

20. A wall, theater or stadium screen incorporating the organic light emitting device of claim 7.

21. A billboard or a sign incorporating the organic light emitting device of claim 7.

22. An organic light emitting device comprising a heterostructure for producing electroluminescence wherein the heterostructure includes a non-metallic cathode comprising a transparent semi-conducting inorganic material in direct contact with a conductive organic layer, wherein the heterostructure for producing electroluminescence is further comprised of, in order,
    an anode layer;
    a hole transporting layer;
    an electron transporting layer;
    a second electron transporting layer;
    an electron injecting interface layer; and
    said non-metallic cathode.

23. The organic light emitting device of claim 22 wherein said second electron transporting layer is comprised of 4,4'-di(N-carbazolo)diphenyl.

24. The organic light emitting device of claim 22 wherein said electron injecting interface layer is comprised of 4,4'-di(N-carbazolo)diphenyl.

25. An organic light emitting device comprising a heterostructure for producing electroluminescence wherein the heterostructure includes a non-metallic cathode comprising a transparent semi-conducting inorganic material in direct contact with a conductive organic layer, wherein the heterostructure for producing electroluminescence is further comprised of, in order,
    an anode layer;
    a hole injection enhancement layer;
    a hole transporting layer;
    an electron transporting layer;
    an electron injecting interface layer; and
    said non-metallic cathode.

26. The organic light emitting device of claim 25 wherein said hole injection enhancement layer is comprised of copper phthalocyanine.

27. A stacked organic light emitting device comprising:
    a first heterostructure for producing electroluminescence, wherein said first heterostructure includes a non-metallic cathode layer comprising a transparent semi-conducting inorganic material in direct contact with a conductive organic layer; and
    a second heterostructure for producing electroluminescence stacked on top of said first heterostructure,
    wherein said transparent semi-conducting inorganic material functions as the anode layer in said second heterostructure.

28. The stacked organic light emitting device of claim 27, wherein said transparent semi-conducting inorganic material comprises indium tin oxide.

29. An organic light emitting device comprising, in order,
    a substrate;
    an anode layer;
    a hole transporting layer;
    a first electron transporting layer;
    a conductive organic layer; and a non-metallic cathode layer;

wherein said non-metallic cathode layer comprises a transparent semi-conducting inorganic material and said non-metallic cathode layer is in direct contact with said conductive organic layer.

30. The organic light emitting device of claim 29 wherein said transparent semi-conducting inorganic material comprises indium tin oxide.

31. The organic light emitting device of claim 30 wherein said substrate is transparent.

32. The organic light emitting device of claim 30 wherein said substrate is flexible.

33. The organic light emitting device of claim 30 wherein said conductive organic layer is an electron transporting material having a carrier mobility of at least $10^{-6}$ cm$^2$/Vsec.

34. The organic light emitting device of claim 30 wherein an emissive layer is present between said electron transporting layer and said hole transporting layer.

35. The organic light emitting device of claim 30 wherein:
  (1) said conductive organic layer comprises a first material having a first ionization potential and a first HOMO/LUMO gap energy; and
  (2) said electron transporting layer comprises a second material having a second ionization potential and a second HOMO/LUMO gap energy;
wherein the difference between the first ionization potential and the first HOMO/LUMO gap energy is not more than about 0.5 eV greater than the difference between the second ionization potential and the second HOMO/LUMO gap energy.

36. The organic light emitting device of claim 35 wherein:
  the difference between the first ionization potential and the first HOMO/LUMO gap energy is equal to or less than the difference between the second ionization potential and the second HOMO/LUMO gap energy.

37. The organic light emitting device of claim 30 wherein said hole transporting layer comprises a hole transporting material selected from the group consisting of N,N'-diphenyl-N,N'-bis(3-methylpheny)1-1'biphenyl-4,4'diamine, 4,4'-bis[N-(1-naphthyl)-N-phenyl-amino]biphenyl and 4,4'-bis[N-(2-naphthyl)-N-phenyl-amino]biphenyl.

38. The organic light emitting device of claim 30 wherein said first electron transporting layer comprises tris-(8-hydroxyquinoline)-aluminum.

39. The organic light emitting device of claim 29 wherein a second electron transporting layer is present between said first electron transporting layer and said conductive organic layer.

40. The organic light emitting device of claim 39 wherein said second electron transporting layer comprises 4,4'-di(N-carbazolo)diphenyl.

41. The organic light emitting device of claim 29 wherein said conductive organic layer comprises a phthalocyanine.

42. The organic light emitting device of claim 41 wherein said phthalocyanine comprises copper phthalocyanine.

43. The organic light emitting device of claim 41 wherein said phthalocyanine comprises zinc phthalocyanine.

44. An organic light emitting device comprising, in order,
  a substrate;
  an anode layer;
  a hole transporting layer;
  a conductive organic layer in direct contact with said hole transporting layer; and
  a non-metallic cathode layer,
wherein said non-metallic cathode layer comprises a transparent semi-conducting inorganic material, and said non-metallic cathode layer is in direct contact with said conductive organic layer.

45. The organic light emitting device of claim 44 wherein said transparent semi-conducting inorganic material comprises indium tin oxide.

46. The organic light emitting device of claim 45 wherein said substrate is transparent.

47. The organic light emitting device of claim 45 wherein said substrate is flexible.

48. The organic light emitting device of claim 45 wherein said conductive organic layer is an electron transporting material having a carrier mobility of at least $10^{-6}$ cm$^2$/Vsec.

49. The organic light emitting device of claim 45 wherein said conductive organic layer is an emissive layer;
  (1) said conductive organic layer comprises a first material having a first ionization potential and a first HOMO/LUMO gap energy; and
  (2) said hole transporting layer comprises a second material having a second ionization potential and a second HOMO/LUMO gap energy;
  wherein the difference between the first ionization potential and the first HOMO/LUMO gap energy is equal to or less than the difference between the second ionization potential and the second HOMO/LUMO gap energy; and
  wherein the second ionization potential is greater than the first ionization potential.

50. The organic light emitting device of claim 45 wherein said hole transporting layer is an emissive layer;
  (1) said conductive organic layer comprises a first material having a first ionization potential and a first HOMO/LUMO gap energy; and
  (2) said hole transporting layer comprises a second material having a second ionization potential and a second HOMO/LUMO gap energy;
  wherein the difference between the first ionization potential and the first HOMO/LUMO gap energy is equal to or less than the difference between the second ionization potential and the second HOMO/LUMO gap energy; and
  wherein the second ionization potential is less than the first ionization potential.

51. The organic light emitting device of claim 45 wherein said hole transporting layer comprises a hole transporting material selected from the group consisting of N,N'-diphenyl-N,N'-bis(3-methylpheny)1-1'biphenyl-4,4'diamine, 4,4'-bis[N-(1-naphthyl)-N-phenyl-amino]biphenyl and 4,4'-bis[N-(2-naphthyl)-N-phenyl-amino]biphenyl.

52. The organic light emitting device of claim 45 wherein said first electron transporting layer comprises tris-(8-hydroxyquinoline)-aluminum.

53. The organic light emitting device of claim 45 wherein said conductive organic layer comprises a phthalocyanine.

54. The organic light emitting device of claim 53 wherein said phthalocyanine comprises copper phthalocyanine.

55. The organic light emitting device of claim 53 wherein said phthalocyanine comprises zinc phthalocyanine.

56. An organic light emitting device comprising, in order,
  a substrate;
  a non-metallic cathode layer;
  a conductive organic layer in direct contact with said non-metallic cathode layer;
  a first electron transporting layer;
  a hole transporting layer; and an anode layer;
wherein said non-metallic cathode layer comprises a transparent semi-conducting inorganic material.

57. The organic light emitting device of claim 56 wherein said transparent semi-conducting inorganic material comprises indium tin oxide.

58. The organic light emitting device of claim 57 wherein said substrate is transparent.

59. The organic light emitting device of claim 57 wherein said substrate is flexible.

60. The organic light emitting device of claim 57 wherein said conductive organic layer is an electron transporting material having a carrier mobility of at least $10^{-6}$ cm$^2$/Vsec.

61. The organic light emitting device of claim 57 wherein:
   (1) said conductive organic layer comprises a first material having a first ionization potential and a first HOMO/LUMO gap energy; and
   (2) said electron transporting layer comprises a second material having a second ionization potential and a second HOMO/LUMO gap energy;
wherein the difference between the first ionization potential and the first HOMO/LUMO gap energy is not more than about 0.5 eV greater than the difference between the second ionization potential and the second HOMO/LUMO gap energy.

62. The organic light emitting device of claim 61 wherein:
   the difference between the first ionization potential and the first HOMO/LUMO gap energy is equal to or less than the difference between the second ionization potential and the second HOMO/LUMO gap energy.

63. The organic light emitting device of claim 57 wherein said hole transporting layer comprises a hole transporting material selected from the group consisting of N,N'-diphenyl-N,N'-bis(3-methylpheny)1-1'biphenyl-4,4'diamine, 4,4'-bis[N-(1-naphthyl)-N-phenyl-amino]biphenyl and 4,4'-bis[N-(2-naphthyl)-N-phenyl-amino]biphenyl.

64. The organic light emitting device of claim 57 wherein said first electron transporting layer comprises tris-(8-hydroxyquinoline)-aluminum.

65. The organic light emitting device of claim 57 wherein said conductive organic layer comprises a phthalocyanine.

66. The organic light emitting device of claim 65 wherein said phthalocyanine comprises copper phthalocyanine.

67. The organic light emitting device of claim 65 wherein said phthalocyanine comprises zinc phthalocyanine.

68. An organic light emitting device comprised of, in order:
   a substrate;
   a non-metallic cathode layer;
   a conductive organic layer in direct contact with said non-metallic cathode layer;
   a first electron transporting layer;
   an emissive layer;
   a hole transporting layer; and
   an anode layer;
wherein said non-metallic cathode layer comprises a transparent semi-conducting inorganic material.

69. An organic light emitting device comprising, in order,
   a substrate;
   a non-metallic cathode layer;
   a conductive organic layer in direct contact with said non-metallic cathode layer;
   a hole transporting layer in direct contact with said conductive layer; and
   an anode layer;
wherein said non-metallic cathode layer comprises a transparent semi-conducting inorganic material.

70. The organic light emitting device of claim 69 wherein said transparent semi-conducting inorganic material comprises indium tin oxide.

71. The organic light emitting device of claim 70 wherein said substrate is transparent.

72. The organic light emitting device of claim 70 wherein said substrate is flexible.

73. The organic light emitting device of claim 70 wherein said conductive organic layer is an electron transporting material having a carrier mobility of at least $10^{-6}$ cm$^2$/Vsec.

74. The organic light emitting device of claim 70 wherein said conductive organic layer is an emissive layer;
   (1) said conductive organic layer comprises a first material having a first ionization potential and a first HOMO/LUMO gap energy; and
   (2) said hole transporting layer comprises a second material having a second ionization potential and a second HOMO/LUMO gap energy;
   wherein the difference between the first ionization potential and the first HOMO/LUMO gap energy is equal to or less than the difference between the second ionization potential and the second HOMO/LUMO gap energy; and
   wherein the second ionization potential is greater than the first ionization potential.

75. The organic light emitting device of claim 70 wherein said hole transporting layer is an emissive layer;
   (1) said conductive organic layer comprises a first material having a first ionization potential and a first HOMO/LUMO gap energy; and
   (2) said hole transporting layer comprises a second material having a second ionization potential and a second HOMO/LUMO gap energy;
   wherein the difference between the first ionization potential and the first HOMO/LUMO gap energy is equal to or less than the difference between the second ionization potential and the second HOMO/LUMO gap energy; and
   wherein the second ionization potential is less than the first ionization potential.

76. The organic light emitting device of claim 70 wherein said hole transporting layer comprises a hole transporting material selected from the group consisting of N,N'-diphenyl-N,N'-bis(3-methylpheny)1-1'biphenyl-4,4'diamine, 4,4'-bis[N-(1-naphthyl)-N-phenyl-amino]biphenyl and 4,4'-bis[N-(2-naphthyl)-N-phenyl-amino]biphenyl.

77. The organic light emitting device of claim 70 wherein said first electron transporting layer comprises tris-(8-hydroxyquinoline)-aluminum.

78. The organic light emitting device of claim 70 wherein said conductive organic layer comprises a phthalocyanine.

79. The organic light emitting device of claim 78 wherein said phthalocyanine comprises copper phthalocyanine.

80. The organic light emitting device of claim 78 wherein said phthalocyanine comprises zinc phthalocyanine.

81. A device comprising an organic light emitting device including a transparent, non-metallic, semi-conductive inorganic material comprising indium tin oxide in direct contact with a conductive organic layer, wherein said semi-conductive inorganic material functions as a cathode in said organic light emitting device wherein said conductive organic layer comprises a phthalocyanine.

82. The organic light emitting device of claim 81 wherein said phthalocyanine comprises copper phthalocyanine.

83. The organic light emitting device of claim 81 wherein said phthalocyanine comprises zinc phthalocyanine.

84. The organic light emitting device of claim 81 wherein said conductive organic layer is an electron transporting material having a carrier mobility of at least $10^{-6}$ cm$^2$/Vsec.

85. A stacked organic light emitting device comprising:
- a first organic light emitting device including a transparent, non-metallic, semi-conductive inorganic material in direct contact with a conductive organic layer, wherein said semi-conductive inorganic material functions as a cathode in said first organic light emitting device;
- a second organic light emitting device stacked on top of said first organic light emitting device, wherein said transparent semi-conducting inorganic material comprises an indium tin oxide layer which functions as an anode in said second organic light emitting device.

86. The stacked organic light emitting device of claim 85 wherein said conductive organic layer comprises a phthalocyanine.

87. The stacked organic light emitting device of claim 86 wherein said phthalocyanine comprises copper phthalocyanine.

88. The stacked organic light emitting device of claim 86 wherein said phthalocyanine comprises zinc phthalocyanine.

89. The stacked organic light emitting device of claim 85 wherein said conductive organic layer is an electron transporting material having a carrier mobility of at least $10^{-6}$ cm$^2$/Vsec.

* * * * *